(12) United States Patent
Ellman et al.

(10) Patent No.: US 6,610,057 B1
(45) Date of Patent: Aug. 26, 2003

(54) ELECTROSURGICAL BLADE ELECTRODE

(76) Inventors: Alan G. Ellman, 1135 Railroad Ave., Hewlett, NY (US) 11557; Jon C. Garito, 1135 Railroad Ave., Hewlett, NY (US) 11557

( * ) Notice: Subject to any disclaimer, the term of this patent is extended or adjusted under 35 U.S.C. 154(b) by 24 days.

(21) Appl. No.: 09/819,017

(22) Filed: Mar. 27, 2001

(51) Int. Cl.[7] ................................................ A61B 18/14
(52) U.S. Cl. ............................. 606/41; 606/45; 606/49
(58) Field of Search ............................. 606/41, 45, 49, 606/29

(56) References Cited

U.S. PATENT DOCUMENTS

| 1,639,996 A | * | 8/1927 | Groff ............................. 606/45 |
| 4,517,975 A | * | 5/1985 | Garito et al. ................. 606/41 |
| 4,754,754 A |   | 7/1988 | Garito |
| 4,960,419 A | * | 10/1990 | Rosenberg ................. 30/296.1 |
| 5,125,927 A | * | 6/1992 | Belanger ...................... 606/45 |
| 5,374,188 A | * | 12/1994 | Frank et al. .................. 606/45 |
| 5,800,427 A | * | 9/1998 | Zamba ......................... 606/39 |
| 5,807,392 A | * | 9/1998 | Eggers ......................... 606/29 |
| 5,954,686 A | * | 9/1999 | Garito et al. ................. 606/40 |

* cited by examiner

*Primary Examiner*—Lee Cohen

(57) ABSTRACT

An improved electrosurgical electrode for removing cancerous tissue and lesions. The electrosurgical electrode comprises a flat round blade having a flat end configured to be held in a scalpel handpiece of the type described in U.S. Pat. No. 4,754,754. The electrode may be formed from a standard disposable scalpel by providing in front a round section whose peripheral edge is sharpened. A modification describes a combined disposable handpiece and electrosurgical electrode.

10 Claims, 3 Drawing Sheets

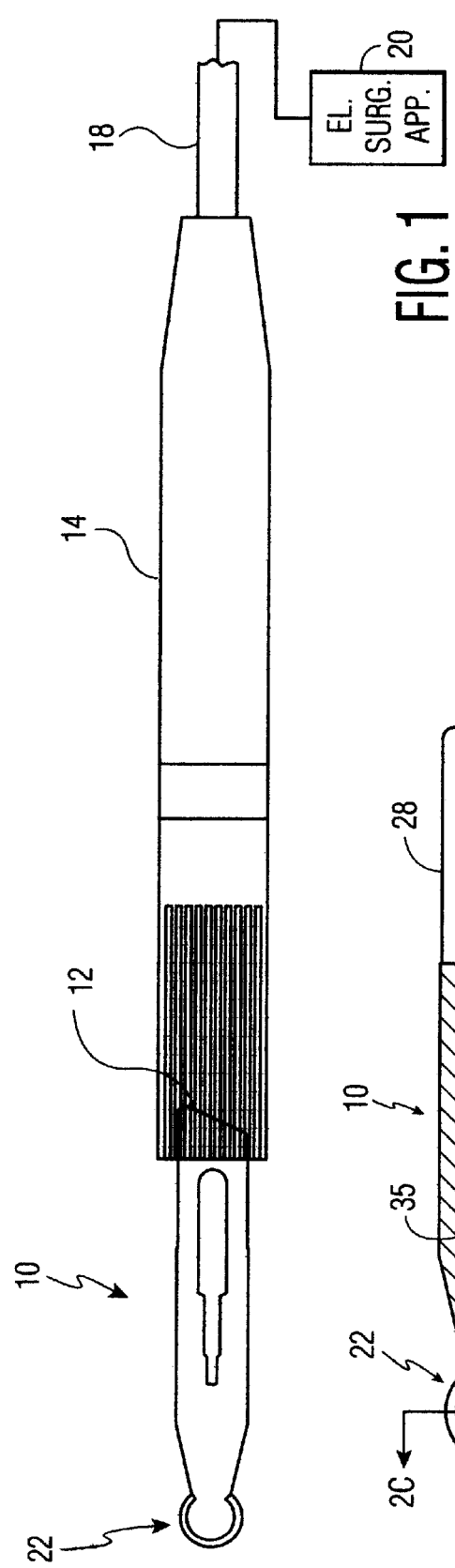
FIG. 1
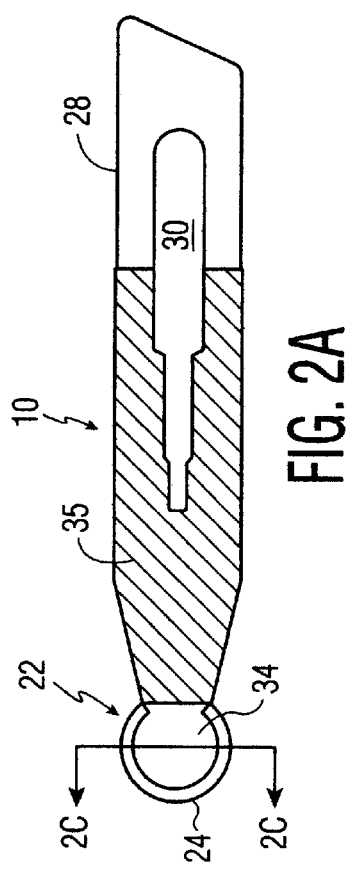
FIG. 2A
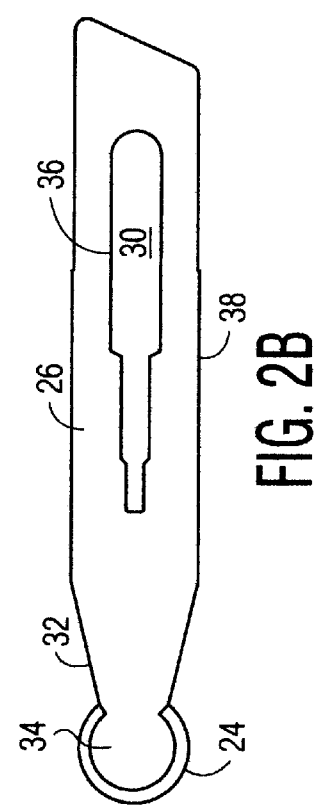
FIG. 2B
FIG. 2C

ELECTROSURGICAL BLADE ELECTRODE

This invention relates to electrosurgery, and in particular to a blade electrode useful in vaporizing lesions and tumor tissues.

BACKGROUND OF THE INVENTION

Electrosurgery is a common procedure for dentists, doctors, and veterinarians. Electrosurgical handpieces are commercially available that will accommodate a wide variety of electrodes shapes and sizes, such as needles, blades, scalpels, balls and wire loops. Also, multi-function electrodes are available. An electrosurgical handpiece for blades is described in U.S. Pat. No. 4,754,754, whose contents are herein incorporated by reference. This is an instrument that can be connected to a source of electrosurgical currents and that provides a slitted collet for receiving the shank of a standard disposable scalpel blade. The instrument can be used in any surgical procedure in which a conventional scalpel is employed, mainly for general cutting procedures. It has the advantage of providing electrosurgical currents at the sharp edge of the scalpel which assist in cutting tissue while at the same time providing a coagulation effect.

Traditionally, thin wire loops and electrosurgery low frequency, highpowered devices were used to cut through tumor tissue such as rhinophymectomy and are a well-known surgical technique and modality. The shortcomings and disadvantages of this surgical method are that wire loop electrode designs are often difficult to use and are often unpredictable and often cause gouging or unwanted deep depth of destruction of adjacent tissue. The curvature of the wire loops can create a deep divot in the tissue, which often delays healing, and results in an uneven skin repair architecture.

An electrosurgical handpiece for blades is described in U.S. Pat. No. 4,754,754, whose contents are herein incorporated by reference. This is an instrument that can be connected to a source of electrosurgical currents and that provides a slitted collet for receiving the shank of a standard disposable scalpel blade. The instrument can be used in many surgical procedures in which a conventional scalpel is employed, mainly for general cutting procedures. It has the advantage of providing electrosurgical currents at the sharp edge of the scalpel which assist in cutting tissue while at the same time providing a coagulation effect. However, the conventional scalpel blade augmented by electrosurgical currents has not traditionally been used for removing cancerous tissue and lesions.

SUMMARY OF THE INVENTION

An object of the invention is an improved electrosurgical electrode for removing cancerous tissue and lesions.

According to one aspect of the invention, an electrosurgical electrode comprises a flat round blade.

According to another aspect of the invention, the electrode is configured to be held in a scalpel handpiece of the type described in U.S. Pat. No. 4,754,754.

According to still another aspect of the invention, the electrode is formed from a standard disposable scalpel by providing in front a round section whose peripheral edge is sharpened.

According to still another aspect of the invention, the slot present in the side of the original scalpel blade, normally used to mount the blade on a conventional scalpel handle, has its edges, normally flat and perpendicular to the plane of the blade, rounded to prevent inadvertent discharge of electrosurgical currents to the tissue surrounding the surgical site.

According to still another aspect of the invention, the round sharp blade is combined with electrosurgical currents at a frequency exceeding 3 MHZ, preferably about 4 MHZ.

According to still another aspect of the invention, the round sharp blade is configured as a permanent part of a disposable handpiece.

Th new round sharp blade of the invention is versatile, and can be used to thoroughly remove cancerous tissue. It's unique design allows 4 MHZ radiofrequency currents to gently smooth and contour skin surfaces after curettage, shave excisions, grafts, flap procedures, and cosmetic removal of benign and malignant lesions. It is excellent in debulking, sculpting scar tissue and sebaceous hyperplasia, and provides a clear, unobstructed visualization of the treated tissue.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components..

BRIEF DESCRIPTION OF THE DRAWINGS

In the drawings:

FIG. 1 is a plan view of one form of electrosurgical electrode according to the invention shown attached to a schematic of the handpiece described in the '754 patent which is in turn electrically connected to electrosurgical apparatus;

FIG. 2A is a top view of the electrosurgical electrode of FIG. 1 separated from the handpiece; hatching has been added to show where an electrically-insulating coating is applied;

FIG. 2B is a view similar to FIG. 2A showing the electrode prior to application of the insulating coating;

FIG. 2C is a cross-sectional view along the line 2C of FIG. 2A;

DETAILED DESCRIPTION OF THE PREFERRED EMBODIMENTS

Figure 3:
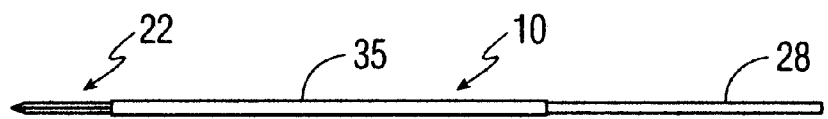
FIG. 3 is a side view of the electrosurgical electrode of FIG. 2A.

U.S. Pat. No. 4,754,754 shows a handpiece of the type capable of receiving a flat blade-type of electrode such as a scalpel. The patent shows that the collet that grips the shank end of the electrode comprises a slot that can receive the flat shank end of the electrode and upon rotation in one direction can grip the electrode and upon rotation in the opposite direction can release the electrode. In the patent, the scalpel's side slot used for mounting is positioned inside of the nosepiece surrounding the collet, which is electrically-conductive, and thus no electrosurgical currents are expected to flow from the slot edges. The blade electrode of the invention, however, has different dimensions with the result that when the shank end is fitted to the collet, as depicted in FIG. 1, the portion of the blade that includes the mounting slot is located outside of the nosepiece and collet, the significance of which will be explained below. It is of course understood that the mounting slot as such has no function in the blade electrosurgical handpiece. It is present because it turns out to be less expensive to fabricate the electrodes of the invention starting from commercially available surgical stainless-steel disposable scalpel blades, which already contain the mounting slot, than to start from a stainless blank.

FIG. 1 is a plan view of a unipolar electrosurgical electrode 10 according to the invention attached to the nosepiece 12 of the hollow handpiece 14 described in the '754 patent. The latter comprises at its end a cable 18 connected at its opposite end to a connector (not shown) for plugging into a standard electrosurgical apparatus 20 supplying electrosurgical currents to the electrode 10 having a working end 22 in the form of a flat round element whose free periphery is sharpened to form a round cutting edge 24. "Round" is used to mean that the working edge that is free of its support has a generally circular geometry. It will be understood that of course it cannot be a 360° circle due to the need for the shank support 26. Inside the nosepiece 12 is a collet (not shown) which receives the uncoated electrically-conductive shank end 28 of the electrode for holding the electrode within the electrosurgical handpiece 14. The cable 18 is electrically connected to the metal collet which in turn is electrically connected to the electrode 10 so that when the electrosurgical apparatus 20 is switched on, electrosurgical currents are supplied to the electrode 10. It is also common for handpiece handles to have switches (not shown) for remote operation of the electrosurgical apparatus.

The electrosurgical apparatus preferably is an ultra high frequency (RF) radiosurgical energy source, which operates in the range of about 3.8–4.0 MHz. Studies have shown that the 3.8–4.0 MHz frequency range is the preferred RF energy to incise and coagulate tissue because tissue thermal necrosis is minimal and, when interfaced with the electrosurgical electrode of the invention, provides excellent cutting and hemostasis especially for removal of cancerous tissue. An example of suitable electrosurgical apparatus is the Model SURGITRON Dual-Frequency electrosurgical unit manufactured by and available from Ellman International, Inc. of Hewlett, N.Y.

The blade electrode 10 of FIG. 1, representing a preferred embodiment of the invention, comprises a flat stamping 26 having a mounting slot 30 (not used in the invention) and which tapers 32 to an uncoated solid circular part 34 whose periphery is sharpened to form the cutting edge 24 of the working end 22. The part of the electrode between the rear shank end 28 and the front circular part 34 is coated on both sides, including the edges, with a thin electrically-insulating coating 35 to prevent any electrical discharges from other than the front circular part 34, which typically will occur at the sharpened edge 24. The uncoated shank end 28 is buried within the handpiece and is not a likely source of electrosurgical currents. The coating 35 in FIG. 2A is shown hatched to distinguish it from the uncoated parts 34, 28.

Since the mounting slot 30 present in the starting stamping typically has perpendicular edges that can be a possible source of electrosurgical currents to regions adjacent the surgical site, it is preferred in accordance with a feature of the invention to round off those edges 36 to prevent such undesirable currents in the event that the coating process has flaws. For similar reasons, the outer edges 38 of the stamping are also rounded.

Figure 4:
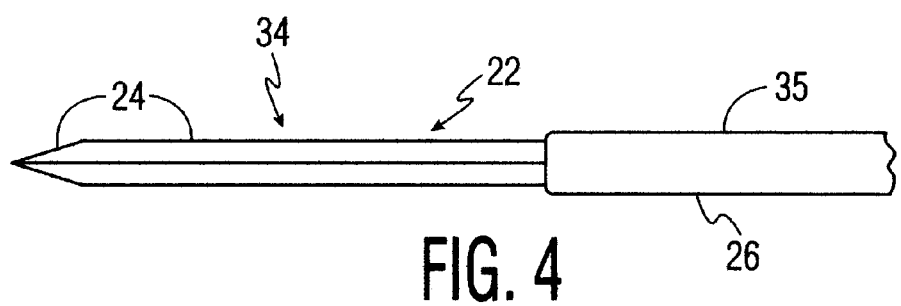
FIG. 4 is an enlarged side view of the working end of the electrosurgical electrode of FIG. 2A.

FIG. 2B shows the stamping of FIG. 2A before the coating with the electrically-insulating coating 35, FIG. 2C is a cross-section across the circular part 34, FIG. 3 is a side view of the electrode of FIG. 2A, and FIG. 4 is an enlarged side view of the working end 22 of the electrode of FIG. 2A.

Figure 5:
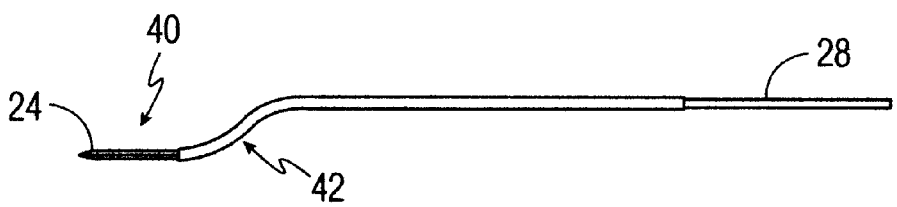
FIG. 5 is a side view of a modification of the electrosurgical electrode according to the invention.
Figure 6:
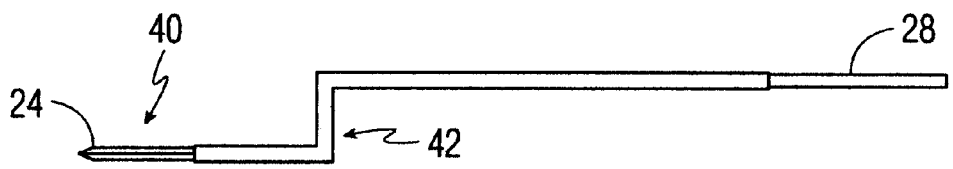
FIG. 6 is an enlarged side view of the working end of another form of electrosurgical electrode according to the invention.

The embodiment of FIGS. 1–4 comprises a straight stamping, meaning a stamping that lies in the same plane. FIGS. 5 and 6 are modifications in which the working end 40 is offset 42 from the shank end 28 either smoothly, sort of spoon-shaped, as in FIG. 5, or abruptly as in FIG. 6 to increase the visibility of the surgical site by the surgeon if desired. The constructions are otherwise the same as that of the first embodiment.

In the operation of the embodiments of the invention, activation of the electrosurgical unit 20 causes the flow of electrosurgical currents from the sharp edge 24 of the electrode working end when applied against or close to the tissue to be destroyed. Controlled vaporization and evaporation of tumor tissue is achieved by using the flat sharp round blade especially with the 4 MHZ radiofrequency apparatus. The cutting current, fully rectified waveform is used. Once the RF is applied, the round knife edge blade is moved across the skin until the desired amount of tissue is vaporized. The design of the novel round sharp blade and its angles allow the flat blade working end to barely touch the skin. The flat knife edge of the blade is typically held parallel to the skin surface and quickly and gently moved from the superior end of the tumor to the inferior end (towards the surgeon) with the knife edge as the leading edge, or can be done in reverse or sideways. The motion is repeated while the electrosurgical currents are flowing from the sharp edge 24 to the tissue until the desired depth of tissue vaporization is achieved. Gently pressing lightly on the skin surface while moving the electrode removes a very thin layer of tissue. Pressing more firmly results in slightly deeper destruction. Moving the round sharp blade briskly results in less tissue damage. Moving slowly across the diseased tissue results in more tissue contact and more destruction. This allows debulking by approaching the raised diseased tissues from the side and smoothly cutting through it undercutting the tissue mass. Alternatively, leaving the flat blade immobile and pressing down with the flat blade surface vaporizes the diseased tissue directly under the RF metal blade surface. The FIGS. 5 and 6 embodiments are especially suitable for this maneuver.

By raising the power (wattage) of the 4 MHz radiosurgery unit the greater the cutting ability and the amount of tissue destruction and vaporization over a unit period of time. There is typically no charring at the higher setting, thus the underlying tissue is readily visualized. This is due to the very low tissue alteration levels of the 4 MHz energy coupled with the fine knife edge of the round sharp blade. The round knife edge also allows the lowest possible power or wattage, which is then focused to permit a finer precise control over the depth of diseased tissue destruction and is excellent for fine tuning and contouring of the skin edges. Another advantage is that tissue smoke plume is greatly reduced using the electrode of the invention. Visibility of the tissue plane can be greatly enhanced by good illumination and magnification with stereoscopic lenses.

There are several surgical advantages to the RF round knife blade electrode. The blade can be used like a spatula enabling the RF energy to sculpt the skin. Another excellent advantage is the precise control of the depth of the excision of the diseased tissue through clear visualization of the remaining char-free tissue after the unwanted diseased tissue has been vaporized. This vaporization technique also allows the surgeon to distinguish the dermis from the deeper dermal tissue. Hair shafts appear as dots. Tissue can be vaporized down through the hair bulbs until only smooth, featureless, deep reticular tissue remains. The RF round sharp blade energized with the 4 MHz radiofrequency energy source gives the surgeon the ability to go further through fat leaving only small amounts of reticular stroma behind. Scar tissue appears white and is easily distinguished from all surrounding tissue. The color and texture difference between the tumor and the normal surrounding tissue are easily discerned.

In addition, moving the RF round sharp blade quickly through the tissue and keeping the wattage power tuned to minimize drag, but not so high as to introduce unnecessary energy, is ideal for minimizing thermal tissue energy. This is particularly helpful with cosmetic concerns where it is important to produce an exact desired amount of tissue destruction. By limiting the tissue destruction depths with the RF round sharp blade to the upper papillary dermis, there is a good chance that the cosmetic results will be quite good. Traditional round loops or curettes destroy tissue beyond appendageal structures and leave the wound to heal by secondary intention pigmentary changes and some scar formation may occur.

A typical length of the electrode 10 is about 1.5 inches long. The uncoated working end typically has a length of about 0.18 inches. The thickness is about 0.015–0.021 inches, and the width at the shank end about 0.236 inches. The radius of the round part is about 0.08–0.1 inches. The electrode coated part 35 is electrically insulated by an appropriate insulating coating 35, which may be of Teflon or ceramic. The electrically insulated part protects the tissue from stray RF leakage energy that could burn unintended areas adjacent the surgical site.

By interfacing the RF tonsil probe with the ultra-high 3.8–4.0 MHZ Radiosurgery apparatus, a number of surgical and clinical advantages, namely: better operative results, due to the high frequency radiosurgery device's ability to significantly reduce tissue necrosis; minimal scarring; reduced surgical pain and post-operative pain; and controlled bleeding and post-operative bleeding.

In summary, true vaporization of diseased tissue utilizing the new RF round sharp blade and 4 MHz radiofrequency energy repetitively moved tangentially across diseased tissue or a tumor offers a number of advantages over traditional electrodesiccation and cold steel curette. This device and method provide excellent visualization of the diseased tissue or tumor bed and surrounding normal tissue. Depth of destruction is easily and precisely controlled by adjusting the amount of power delivered, the blade angle, along with varying the speed and pressure of each pass. This RF round sharp blade is highly versatile and affords either a rapid, extensive destruction of tissue debulking as in basal cell carcinoma removals, scar debulking, rhinophyma reduction, more delicate cosmetic tissue contouring and layering as in smoothing out the skin borders of graft and flap repairs or leveling off a nevus after a shave excision.

The new blade electrode has several configurations which offer accessibility to all tissue and skin architecture and anatomy. A first is the right angle offset of FIG. 6. A second is the spoon curved offset of FIG. 5. An additional feature is the use of a baked Teflon coating of the shaft up to the round part to protect from unwanted RF energy touching areas of the skin or anatomy that is not being treated. This Teflon coating further enhances the focus of the RF energy to the sharp knife edge of the blade.

The round sharp blade can be made in a variety of metals such as stainless steel, tungsten, brass, berylium and the like, stainless steel being preferred. It can be easily made in a typical and well-known stamping operation. This is an important advantage because it allows the new blade to be made very inexpensively thus making it highly affordable to all surgeons. It can be made in a sterile disposable single use design but it is not limited to single use. It can also be made in reusable autoclaveable material.

Figure 7:
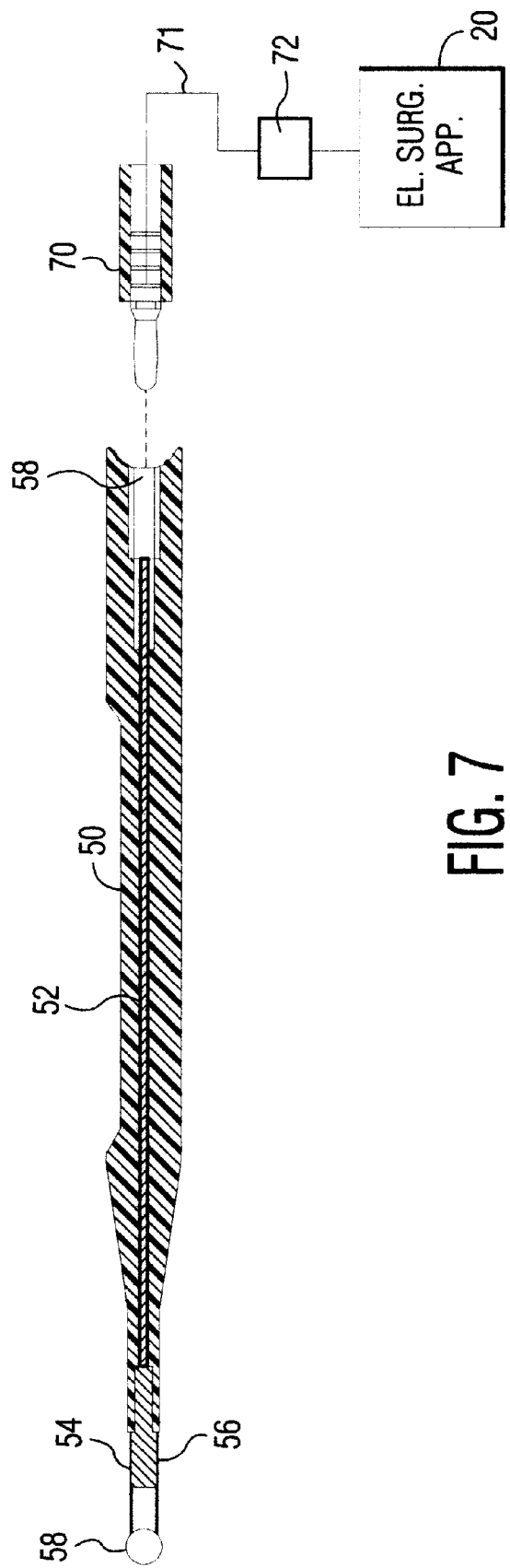
FIG. 7 is a plan view of a disposable form of electrosurgical handpiece according to the invention.

The embodiments of FIGS. 1–6 disclose a removable blade electrode for use in a reusable handpiece of the type disclosed in the '754 patent. FIG. 7 shows an embodiment in which the blade electrode is made a permanent part of a disposable handpiece to which an electric cable may be removably connected and thus preserved for reuse with other disposable or non-disposable handpieces. In the FIG. 7 embodiment, the handpiece 50 is constituted of electrically-insulating material, such as plastic, through the center of which passes an electrically-conductive wire or tube 52 which at the left end is permanently connected as by welding or soldering to a flat blade 54 similar to the of FIG. 2A except that the entire blade is coated with an electrically-insulating material 56 except for the round sharp working end 58. Thus, extending from the working end 58 all the way back to the right end of the handpiece is protected by electrically-insulating material 50, 56. The right end contains a bore 58 whose interior is electrically-conductive and which is configured to removably receive a banana-type plug 70. The latter in turn is connected to a standard cable 71 terminating in a standard plug 72 adapted to be plugged into the unipolar socket of the electrosurgical apparatus 20. Thus, the cable can be disconnected from the handpiece 50 and reused with other disposable handpieces. In this embodiment, the blade electrode 54 is permanently a part of the handpiece 50 and cannot be removed. If the entire handpiece with blade is made of sterilizable material, then it can be sterilized after use and reused. However, the plastic molded construction of the handpiece makes for an inexpensive part to which the metal blade, internal wire, and banana receptacle are also inexpensively added, making for a rather inexpensive disposable part. The cable, which cannot usually be sterilized, and which may be the more expensive of all the parts, can be reused.

Other variations in the shape of the electrosurgical electrode working end while retaining its benefits and advantages will be evident to those skilled in the art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A unipolar electrosurgical electrode comprising:
   a) an elongated blade-like body having an electrically-conductive first end portion for removably attaching to the nosepiece of an electrosurgical handpiece,
   b) said elongated body having at a second end an active electrosurgical end in the form of a blade capable of supplying electrosurgical currents when the first end portion is connected to electrosurgical apparatus, the second end being connected by a narrower necked-down portion to the first end portion, c) said active electrosurgical end comprising a generally flat round bare part having first and second opposed flat sides and having along a front portion of its periphery, projecting forwardly of the round part in a direction away from the first end, an exposed sharpened edge, d) the first flat side of the active electrosurgical end being bare and uncoated to allow electrosurgical currents to flow to tissue underneath when the first flat side is placed near or in contact with the tissue and moved tangentially across or pressed down into the tissue.

2. An electrosurgical electrode as set forth in claim 1, wherein the narrower necked-down portion and part of the adjacent electrode up to the first end portion of the electrode are coated with an electrically-insulating coating.

3. An electrosurgical electrode as set forth in claim 1, wherein the body is a one-piece metal stamping and the length of the active electrosurgical end is about 0.18 inches.

4. An electrosurgical electrode as set forth in claim 1, wherein the blade-like body has a mounting slot extending axially between the first end portion and the active electrosurgical end.

5. An electrosurgical electrode as set forth in claim 4, wherein the edges of the mounting slot are rounded.

6. An electrosurgical electrode as set forth in claim 1, wherein the first end portion and second end and the necked-down portion all lie in the same plane.

7. An electrosurgical electrode as set forth in claim 1, wherein the second end is offset from the first end portion and both ends lie in non-common parallel planes.

8. An electrosurgical electrode as set forth in claim 1, wherein the elongated body is everywhere, except for the first end portion and the second end including the sharpened edge, coated with an electrically-insulating layer.

9. A procedure for excising diseased tissue comprising:
(a) providing an electrosurgical electrode comprising:
  i) an elongated blade-like body having an electrically-conductive first end portion for removably attaching to the nosepiece of an electrosurgical handpiece,
  ii) said elongated body having at a second end an active electrosurgical end in the form of a blade capable of supplying electrosurgical currents when the first end portion is connected to electrosurgical apparatus, the second end being connected by a narrower necked-down portion to the first end portion,
  iii) said active electrosurgical end comprising a generally flat round bare part having first and second opposed flat sides and having along a front portion of its periphery, projecting forwardly of the round part in a direction away from the first end, an exposed sharpened edge,
  iv) the first flat side of the active electrosurgical end being bare and uncoated to allow electrosurgical currents to flow to tissue underneath when the first flat side is placed near or in contact with the tissue,
(b) connecting the electrosurgical electrode to electrosurgical apparatus and activating the apparatus,
(c) holding the first flat side of the active electrosurgical end parallel to the tissue surface and moving it with the sharpened edge in front tangentially across the diseased tissue while vaporizing layers of the diseased tissue, or leaving the flat round part immobile and pressing down on the tissue with its first flat side to vaporize diseased tissue directly under the flat surface.

10. A procedure for excising diseased tissue as set forth in claim 9, further comprising providing a source of electrosurgical currents having a frequency in the range of about 3.8–4.0 MHz, wherein the electrosurgical currents are applied to the active electrosurgical end during at least part of the time that step (c) is carried out.

* * * * *